United States Patent
Jang et al.

(10) Patent No.: US 9,901,904 B2
(45) Date of Patent: Feb. 27, 2018

(54) SUPERABSORBENT POLYMER AND PREPARATION METHOD THEREOF

(71) Applicant: LG Chem, Ltd., Seoul (KR)

(72) Inventors: Tae Hwan Jang, Daejeon (KR); Seong Beom Heo, Daejeon (KR); Mi Young Kim, Daejeon (KR); Min Gyu Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/104,485

(22) PCT Filed: Nov. 24, 2015

(86) PCT No.: PCT/KR2015/012664
§ 371 (c)(1),
(2) Date: Jun. 14, 2016

(87) PCT Pub. No.: WO2016/104962
PCT Pub. Date: Jun. 30, 2016

(65) Prior Publication Data
US 2016/0361703 A1    Dec. 15, 2016

(30) Foreign Application Priority Data

Dec. 22, 2014 (KR) .......................... 10-2014-0186252
Oct. 7, 2015 (KR) .......................... 10-2015-0140933

(51) Int. Cl.
*B01J 20/26* (2006.01)
*C08J 3/24* (2006.01)
(Continued)

(52) U.S. Cl.
CPC ............. *B01J 20/267* (2013.01); *A61L 15/60* (2013.01); *B01J 20/103* (2013.01);
(Continued)

(58) Field of Classification Search
CPC ....................................................... B01J 20/26
(Continued)

(56) References Cited

U.S. PATENT DOCUMENTS

| 4,446,261 A | 5/1984 | Yamasaki et al. |
| 5,149,335 A | 9/1992 | Kellenberger et al. |

(Continued)

FOREIGN PATENT DOCUMENTS

| CN | 102361890 A | 2/2012 |
| CN | 102844340 A | 12/2012 |

(Continued)

OTHER PUBLICATIONS

International Search Report from PCT/KR2015/012664, dated Feb. 23, 2016.
(Continued)

*Primary Examiner* — Duc Truong
(74) *Attorney, Agent, or Firm* — Lerner, David, Littenberg, Krumholz & Mentlik, LLP (57) ABSTRACT

Provided are a superabsorbent polymer and a preparation method thereof. The superabsorbent polymer according to the present invention has excellent gel bed permeability (GBP) and suction power, thereby being usefully applied to hygiene products such as diapers.

12 Claims, 5 Drawing Sheets

(51) Int. Cl.
  *C08J 3/075* (2006.01)
  *A61L 15/60* (2006.01)
  *C08F 2/48* (2006.01)
  *C08F 6/00* (2006.01)
  *B01J 20/10* (2006.01)
  *B01J 20/28* (2006.01)
  *C08F 220/06* (2006.01)
  *A61L 15/00* (2006.01)
  *C08F 20/10* (2006.01)

(52) U.S. Cl.
  CPC .......... *B01J 20/28011* (2013.01); *C08F 2/48* (2013.01); *C08F 6/008* (2013.01); *C08F 220/06* (2013.01); *C08J 3/075* (2013.01); *C08J 3/245* (2013.01); *B01J 2220/68* (2013.01); *C08J 2333/02* (2013.01)

(58) Field of Classification Search
  USPC ......................................................... 528/87
  See application file for complete search history.

(56) References Cited

U.S. PATENT DOCUMENTS

| | | |
|---|---|---|
| 7,179,851 B2 | 2/2007 | Qin et al. |
| 8,420,567 B1 | 4/2013 | Naumann et al. |
| 2008/0058747 A1 | 3/2008 | Singh Kainth et al. |
| 2010/0099781 A1 | 4/2010 | Tian et al. |
| 2010/0247916 A1 | 9/2010 | Hamilton et al. |
| 2012/0289671 A1 | 11/2012 | Takaai et al. |
| 2012/0309619 A1 | 12/2012 | Kwon et al. |
| 2013/0299739 A1 | 11/2013 | Grill et al. |
| 2015/0011388 A1 | 1/2015 | Matsumoto et al. |
| 2015/0093575 A1 | 4/2015 | Naumann et al. |
| 2015/0099624 A1 | 4/2015 | Lee et al. |

FOREIGN PATENT DOCUMENTS

| | | | |
|---|---|---|---|
| EP | 0450922 A2 | 10/1991 | |
| EP | 0605150 A1 | 7/1994 | |
| EP | 0668080 A2 | 8/1995 | |
| EP | 2837641 | * 2/2015 | ............. B01J 20/26 |
| JP | 56-161408 A | 12/1981 | |
| JP | S57158209 A | 9/1982 | |
| JP | 57-198714 A | 12/1982 | |
| JP | 2010116548 A | 5/2010 | |
| JP | 5504334 B2 | 5/2014 | |
| KR | 19960008111 B1 | 6/1996 | |
| KR | 20090042828 A | 4/2009 | |
| KR | 20110087293 A | 8/2011 | |
| KR | 20110111943 A | 10/2011 | |
| KR | 20140063400 A | 5/2014 | |
| KR | 20140102264 A | 8/2014 | |
| KR | 20140107491 A | 9/2014 | |
| KR | 20140125420 A | 10/2014 | |
| WO | 9511932 A1 | 5/1995 | |
| WO | 2004096304 A1 | 11/2004 | |
| WO | 2005016393 A1 | 2/2005 | |

OTHER PUBLICATIONS

Odian, George, "Principles of Polymerization," Second Edition, A Wiley-Interscience Publication, John Wiley & Sons, 1981, p. 203.
Schwalm, Reinhold, "UV Coatings: Basics, Recent Developments and New Applications." Elsevier Science, Dec. 21, 2006, p. 115.
Extended European Search Report for Application No. EP15864314 dated Jul. 3, 2017.
Third Party Observation for EP15864314.8 dated Apr. 21, 2017.
Third Party Observation for PCT/KR2015/012664 submitted Apr. 20, 2017.

* cited by examiner

SUPERABSORBENT POLYMER AND PREPARATION METHOD THEREOF

CROSS-REFERENCE TO RELATED APPLICATION

The present application is a national phase entry under 35 U.S.C. § 371 of International Application No. PCT/KR2015/012664, filed Nov. 24, 2015, which claims priority from Korean Patent Application No. 10-2014-0186252 filed Dec. 22, 2014, and Korean Patent Application No. 10-2015-0140933 filed Oct. 7, 2015, the disclosures of which are incorporated herein by reference.

TECHNICAL FIELD

The present disclosure relates to a superabsorbent polymer having excellent gel bed permeability (GBP) and suction power, and a preparation method thereof.

BACKGROUND ART

A superabsorbent polymer (SAP) is a type of synthetic polymeric materials capable of absorbing moisture from about 500 to 1000 times its own weight, and also called SAM (Super Absorbency Material), AGM (Absorbent Gel Material), etc. Since superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields or the like.

As a preparation process for such superabsorbent polymers, a process by a reverse phase suspension polymerization and a process by a solution polymerization have been known. Of them, preparation of the superabsorbent polymer by reverse phase suspension polymerization is disclosed in, for example, Japanese Patent Laid-open Publication Nos. S56-161408, S57-158209, S57-198714, etc. Further, preparation of the superabsorbent polymer by the solution polymerization further includes a thermal polymerization method in which a water-containing gel polymer is polymerized while being broken and cooled in a kneader equipped with a plurality of shafts, and a photo-polymerization method in which an aqueous solution with a high concentration is irradiated with UV rays onto a belt to be polymerized and dried at the same time.

Important performances of hygiene products such as diapers, etc. are intake time and wet back. As diapers become thinner, permeability is also emerging as an important performance for efficient diffusion of a material absorbed into the superabsorbent polymer used in diapers. For better dryness of diapers, it is important to improve suction power of sucking urine from pulps.

To improve gel bed permeability, a method of increasing the degree of internal crosslinking or gel strength of the superabsorbent polymer or a method of coating the surface thereof with silica or inorganic particles is known. On the contrary, to improve suction power, the degree of internal crosslinking of the superabsorbent polymer must be decreased and the content of silica or inorganic particles on the surface thereof must be decreased.

In the prior art, however, there have been problems that increase of the silica coating for improvement of gel bed permeability of the superabsorbent polymer decreases absorbency under load and suction power. Accordingly, there is an urgent demand for a preparation method capable of improving gel bed permeability, absorbency under load, and suction power at the same time.

DISCLOSURE

Technical Problem

The present invention is intended to provide a superabsorbent polymer having excellent suction power and gel bed permeability.

Further, the present invention is intended to provide a method of preparing the superabsorbent polymer.

Technical Solution

In order to achieve the above objects, the present invention provides a superabsorbent polymer as follows:

(1) the super absorbent polymer, including a base polymer including a crosslinked polymer of water-soluble ethylene-based unsaturated monomers having acidic groups which are at least partially neutralized, and a surface crosslinked layer including the additionally crosslinked polymer of the base polymer, which is formed on the base polymer, in which suction power of 1 g of the superabsorbent polymer for 5 minutes is 13 mL/g or more and gel bed permeability (GBP) of the superabsorbent polymer is 41 Darcy or more.

As hygiene products such as diapers, etc. become thinner, permeability is also emerging as an important performance for efficient diffusion of a material absorbed into the superabsorbent polymer used in diapers. Gel bed permeability is one of factors for evaluating permeability. Conventionally, to improve gel bed permeability, a method of coating the surface of the superabsorbent polymer with silica or inorganic particles has been used. According to this method, gel bed permeability of the superabsorbent polymer is improved. However, there have been problems that increase of the coating amount deteriorates other important properties of the superabsorbent polymer, such as absorbency under load and suction power. Particularly, when suction power is decreased, the superabsorbent polymer exhibits low ability to suck a material absorbed into hygiene products such as diapers, etc., resulting in poor dryness of hygiene products.

Therefore, the present invention is characterized by providing a superabsorbent polymer having improved gel bed permeability and absorbency under load as well as improved suction power by increasing surface crosslinking density of the superabsorbent polymer when the surface of the superabsorbent polymer is coated with silica particles.

Suction power (SP) of 1 g of the superabsorbent polymer for 5 minutes may be measured by the following method.

Figure 5:
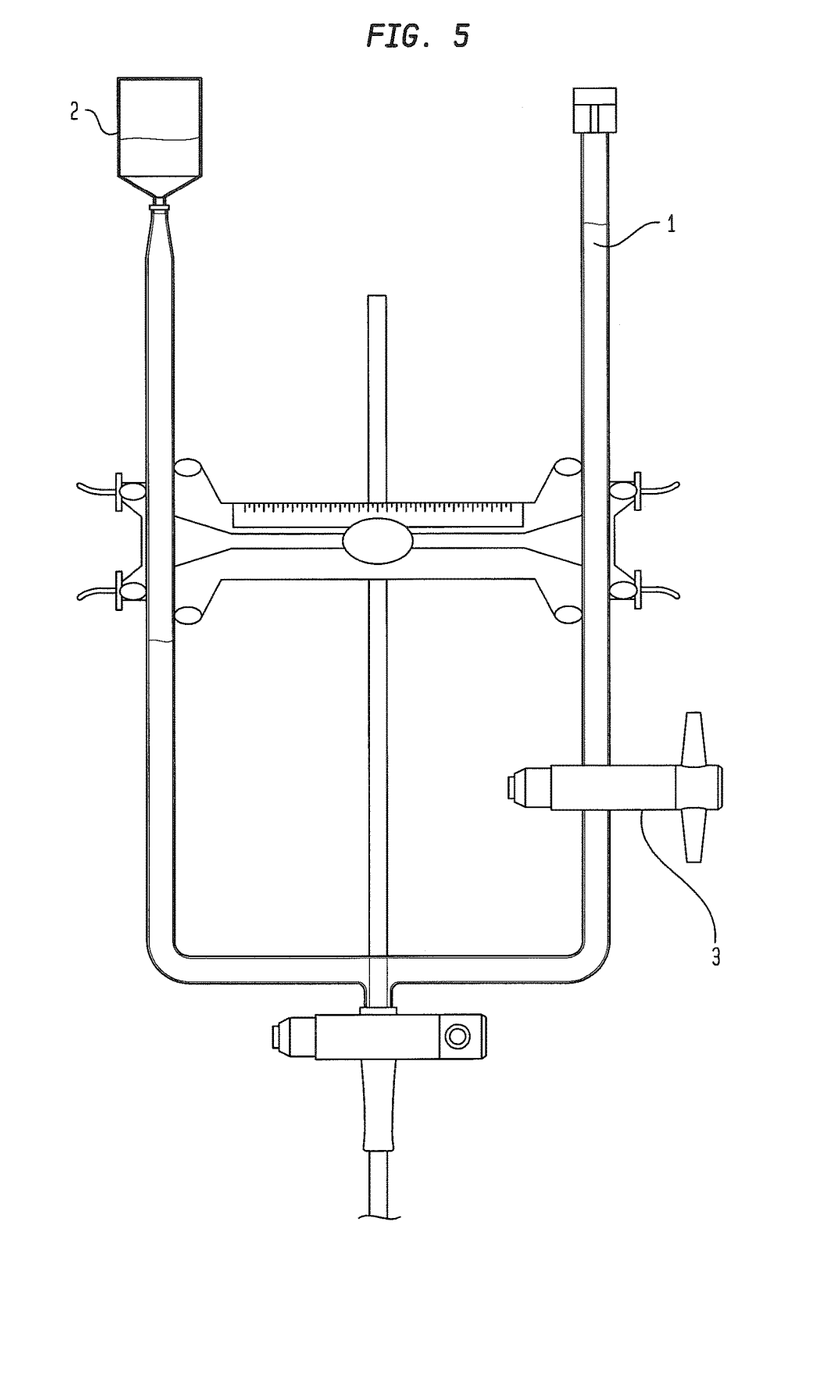
FIG. 5 illustrates an example of an apparatus for measuring suction power according to an embodiment of the present invention.

A saline solution (0.9% NaCl) is poured to 0 ml graduation mark of a glass tube having an internal diameter of 20 mm on the right of a measuring device as in FIG. 5. A 100-micrometer glass filter is placed on the bottom of a cylindrical funnel having an internal diameter of 50 mm on the left of the measuring device, and 1.0 g of the superabsorbent polymer is uniformly scattered on the glass filter at 23° C. and the relative humidity of 50%. While the superabsorbent polymer is scattered, the amount of saline solution absorbed into 1 g of the superabsorbent polymer for 5 minutes is measured by opening a tap of a burette of the measuring device.

The suction power (SP) of the superabsorbent polymer of the present invention which is measured according to the above method may be preferably 13.2 mL/g or more, 13.4 mL/g or more, 13.6 mL/g or more, 13.8 mL/g or more, 14.0 mL/g or more, 14.2 mL/g or more, 14.4 mL/g or more, 14.6 mL/g or more, 14.8 mL/g or more, or 15.0 mL/g or more. As the suction power is higher, the physical properties of the superabsorbent polymer are more improved. There is no upper limit, but the suction power may be, for example, 18.0 mL/g or less, 17.8 mL/g or less, 17.6 mL/g or less, 17.4 mL/g or less, 17.2 mL/g or less, or 10.0 mL/g or less.

(2) Further, the present invention provides a superabsorbent polymer, in which the superabsorbent polymer of (1) has gel bed permeability (GBP) of 41 Darcy or more.

The gel bed permeability (GBP) is expressed in "Darcy" which is a CGS unit of permeability. For example, one Darcy is the permeability of a solid through which 1 cm$^3$ of fluid, having a viscosity of 1 cps, will flow in 1 second through a section 1 cm in thickness and 1 cm$^2$ in cross-section area, if the pressure difference between the two sides of the solid is one atmosphere. Permeability has the same units as area, since there is no SI unit of permeability, m$^2$ are used. One Darcy is equal to about 0.98692×10$^{12}$ m$^2$ or about 0.98692×10$^{-8}$ cm$^2$. A method of measuring the gel bed permeability is described in U.S. Pat. No. 7,179,851. The gel bed permeability (GBP) determines the permeability of a swollen bed of gel particles (e.g., absorbent materials after surface treatment or absorbent materials before surface treatment) under what is commonly referred to as "free swell" conditions.

The gel bed permeability (GBP) of the superabsorbent polymer according to the present invention may be preferably 45 Darcy or more, 50 Darcy or more, 55 Darcy or more, 60 Darcy or more, 65 Darcy or more, 70 Darcy or more, 75 Darcy or more, 80 Darcy or more, 85 Darcy or more, 90 Darcy or more, 95 Darcy or more, 100 Darcy or more, 105 Darcy or more, 110 Darcy or more, 115 Darcy or more, or 120 Darcy or more. Further, as the gel bed permeability is higher, the physical properties of the superabsorbent polymer are more improved. There is no upper limit, but the gel bed permeability may be, for example, 150 Darcy or less, 145 Darcy or less, 140 Darcy or less, or 135 Darcy or less.

(3) Further, the present invention provides a superabsorbent polymer, in which the superabsorbent polymer of (1) or (2) has absorbency under load (AUL) at 0.9 psi of 17.3 g/g or more.

The absorbency under load (AUL) at 0.9 psi may be represented by the following Equation 1:

$$AUL(g/g)=[Wb(g)-Wa(g)]/\text{the weight (g) of the superabsorbent polymer}$$ [Equation 1]

wherein,

Wa(g) is the sum (g) of the weight of the superabsorbent polymer and the weight of the apparatus capable of providing a load for the superabsorbent polymer, and Wb(g) is the sum (g) of the weight of the water-absorbed superabsorbent polymer after supplying water for the superabsorbent polymer under a load (0.9 psi) for 60 minutes and the weight of the apparatus capable of providing a load for the superabsorbent polymer.

The superabsorbent polymer according to the present invention may have absorbency under load (AUL) at 0.9 psi of 17.5 g/g or more, 18.0 g/g or more, 18.5 g/g or more, 19.0 g/g or more, 19.5 g/g or more, 20.0 g/g or more, 20.5 g/g or more, 21.0 g/g or more, or 21.5 g/g or more. Further, as the absorbency under load (AUL) at 0.9 psi is higher, the physical properties of the superabsorbent polymer are more improved. There is no upper limit, but the absorbency under load (AUL) at 0.9 psi may be, for example, 25 g/g or less, 24 g/g or less, or 23 g/g or less.

(4) In the superabsorbent polymer of any one of (1) to (3), the water-soluble ethylene-based unsaturated monomer may be any monomer which is generally used in the preparation of the superabsorbent polymer. A non-limiting example of the water-soluble ethylene-based unsaturated monomer may be a compound represented by the following Chemical Formula 1:

[Chemical Formula 1]

wherein, $R_1$ is an alkyl group containing an unsaturated bond and having 2 to 5 carbon atoms, and $M^1$ is a hydrogen atom, a monovalent or divalent metal, an ammonium group, or an organic amine salt.

(5) Preferably, in the superabsorbent polymer of any one of (1) to (3), the water-soluble ethylene-based unsaturated monomer may be one or more selected from the group consisting of acrylic acid, methacrylic acid, and a monovalent metal salt, a divalent metal salt, an ammonium salt, and an organic amine salt thereof.

As such, when acrylic acid or a salt thereof is used as the water-soluble ethylene-based unsaturated monomer, it is advantageous in that a superabsorbent polymer having improved absorbency is obtained. In addition, as the monomer, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, (meth)acrylamide, N-substituted (meth)acrylate, 2-hydroxyethyl (meth)acrylate, 2-hydroxypropyl(meth)acrylate, methoxy polyethylene glycol(meth)acrylate, polyethylene glycol (meth)acrylate, (N,N)-dimethylaminoethyl(meth)acrylate, or (N,N)-dimethylaminopropyl(meth)acrylate may be used.

Here, the water-soluble ethylene-based unsaturated monomers may be those having acidic groups which are at least partially neutralized. Preferably, the monomers may be those partially neutralized with an alkali substance such as sodium hydroxide, potassium hydroxide, ammonium hydroxide or the like.

In this regard, a degree of neutralization of the monomer may be about 40 mole % to 95 mole %, about 40 mole % to 80 mole %, or about 45 mole % to 75 mole %. The range of the neutralization degree may vary depending on the final physical properties. An excessively high degree of neutralization renders the neutralized monomers precipitated, and thus polymerization may not occur readily, whereas an excessively low degree of neutralization not only deteriorates the absorbency of the polymer but also endows the polymer with hard-to-handle properties, such as of elastic rubber.

The surface crosslinking is a method of increasing the crosslinking density of the surface of the polymer particles, and a crosslinking agent and a surface crosslinking method used for the surface crosslinking will be described below.

Method of Preparing the Superabsorbent Polymer

Further, the present invention provides a method of preparing the above-described superabsorbent polymer, the method including the following steps of:

1) performing thermal polymerization or photo-polymerization of a monomer composition including water-soluble ethylene-based unsaturated monomers and a polymerization initiator to form a water-containing gel polymer, 2) drying the water-containing gel polymer, 3) pulverizing the dried polymer, and 4) surface-crosslinking the pulverized polymer by reacting the pulverized polymer with a compound having two or more epoxy rings at 170° C. to 250° C. for 50 minutes or longer.

Hereinafter, each step of the present invention will be described in detail.

Step of Forming the Water-Containing Gel Polymer (Step 1)

First, the method of preparing the superabsorbent polymer includes the step of performing thermal polymerization or photo-polymerization of a monomer composition including water-soluble ethylene-based unsaturated monomers and a polymerization initiator to form a water-containing gel polymer.

The water-soluble ethylene-based unsaturated monomers included in the monomer composition are the same as described above. Further, the concentration of the water-soluble ethylene-based unsaturated monomer in the monomer composition may be properly controlled, in consideration of polymerization time and reaction conditions, and the concentration may be preferably 20% by weight to 90% by weight, or 40% by weight to 65% by weight, which is for using the gel effect during the polymerization reaction in a high-concentration aqueous solution to eliminate a need for removing the unreacted monomer after the polymerization and also for improving pulverization efficiency upon a subsequent pulverization process of the polymer. However, if the concentration of the monomer is too low, the yield of the superabsorbent polymer may become low. On the contrary, if the concentration of the monomer is too high, there is a process problem that a part of the monomers is precipitated, or pulverization efficiency is lowered upon pulverization of the polymerized water-containing gel polymer, and the physical properties of the superabsorbent polymer may be reduced.

Meanwhile, the monomer composition may include a polymerization initiator generally used in the preparation of the superabsorbent polymer. Non-limiting examples of the polymerization initiator may include a thermal polymerization initiator or a photo-polymerization initiator depending on a polymerization method. However, even though the photo-polymerization is performed, a certain amount of heat is generated by UV irradiation or the like and is also generated with exothermic polymerization reaction. Therefore, the thermal polymerization initiator may be further included.

Here, the photo-polymerization initiator may be, for example, one or more compounds selected from the group consisting of benzoin ether, dialkyl acetophenone, hydroxyl alkylketone, phenyl glyoxylate, benzyl dimethyl ketal, acyl phosphine, and α-aminoketone. As the specific example of acyl phosphine, commercial Lucirin® TPO, namely, 2,4,6-trimethyl-benzoyl-trimethyl phosphine oxide, may be used. More various photo-polymerization initiators are well disclosed in "UV Coatings: Basics, Recent Developments and New Applications" written by Reinhold Schwalm, (Elsevier, 2007), p115, which may be served as a reference.

Further, the thermal polymerization initiator may be one or more compounds selected from the group consisting of persulfate-based initiators, azo-based initiators, hydrogen peroxide, and ascorbic acid. Specific examples of the persulfate-based initiators may include sodium persulfate ($Na_2S_2O_8$), potassium persulfate ($K_2S_2O_8$), ammonium persulfate (($NH_4$)$_2S_2O_8$) or the like. Further, specific examples of the azo-based initiators may include 2,2-azobis(2-amidinopropane)dihydrochloride, 2,2-azobis-(N,N-dimethylene) isobutyramidine dihydrochloride, 2-(carbamoylazo)isobutylonitril, 2,2-azobis(2-[2-imidazolin-2-yl]propane) dihydrochloride, 4,4-azobis-(4-cyanovaleric acid) or the like. More various thermal polymerization initiators are well-disclosed in "Principle of Polymerization" written by Odian, (Wiley, 1981), p203, which may be served as a reference.

The polymerization initiator may be added at a concentration of about 0.001% by weight to 1% by weight, based on the monomer composition. That is, if the concentration of the polymerization initiator is too low, the polymerization rate becomes low and thus a large amount of residual monomers may be undesirably extracted from the final product. On the contrary, if the concentration of the polymerization initiator is too high, the polymer chains constituting the network becomes short, and thus the content of water-soluble components is increased and physical properties of the polymer may deteriorate such as a reduction in absorbency under load.

Meanwhile, the monomer composition may further include a crosslinking agent ("internal crosslinking agent") to improve physical properties of the polymer by polymerization of the water-soluble ethylene-based unsaturated monomer. The crosslinking agent is used for internal cross-linking of the water-containing gel polymer, and separately used, independent of a crosslinking agent ("surface crosslinking agent") for surface crosslinking of the water-containing gel polymer.

As the internal crosslinking agent, any internal crosslinking agent having a crosslinkable functional group which is generally used in the preparation of the superabsorbent polymer may be used without limitation. However, to further improve physical properties of the superabsorbent polymer, a multifunctional acrylate-based compound having a plurality of ethylene oxide groups may be used as the internal crosslinking agent. More specific examples of the internal crosslinking agent may include one or more selected from the group consisting of polyethylene glycol diacrylate (PEGDA), glycerin diacrylate, glycerin triacrylate, non-modified or ethoxylated trimethylol propane triacrylate (TMPTA), hexanediol diacrylate, and triethylene glycol diacrylate.

The internal crosslinking agent may be added in an amount of about 0.001% by weight to 1% by weight, based on the monomer composition. If the concentration of the internal crosslinking agent is too low, the polymer may have low absorption rate and low gel strength, undesirably. On the contrary, if the concentration of the internal crosslinking agent is too high, the polymer may have low absorption ability, which is not preferred as an absorbent.

In addition, the monomer composition may further include an additive such as a thickener, a plasticizer, a preservation stabilizer, an antioxidant, etc., if necessary.

Further, the raw materials such as the above-described monomers, polymerization initiator, internal crosslinking agent, etc. may be prepared in the form of a solution of the monomer composition which is dissolved in a solvent.

In this regard, as the solvent, any solvent may be used without limitations in the constitution, as long as it is able to dissolve the above raw materials. For example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof may be used as the solvent.

The formation of the water-containing gel polymer by polymerizing the monomer composition may be performed by a general polymerization method, and the process is not particularly limited. A non-limiting example of the polymerization method is largely classified into the thermal polymerization and the photo-polymerization according to the polymerization energy source, and the thermal polymerization may be carried out in a reactor like a kneader equipped with agitating spindles and the photo-polymerization may be carried out in a reactor equipped with a movable conveyor belt.

For example, the monomer composition is injected to a reactor like a kneader equipped with the agitating spindles, and thermal polymerization is performed by providing hot air thereto or heating the reactor so as to obtain the water-containing gel polymer. In this regard, the water-containing gel polymer may have the size of centimeters or millimeters when it is discharged from the outlet of the reactor, according to the type of agitating spindles equipped in the reactor. Specifically, the water-containing gel polymer may be obtained in various forms according to the concentration of the monomer composition fed thereto, the feeding speed or the like, and the water-containing gel polymer having a (weight average) particle diameter of 2 to 50 mm may be generally obtained.

Further, when the photo-polymerization of the monomer composition is carried out in a reactor equipped with a movable conveyor belt, the water-containing gel polymer may be obtained in a sheet-type. In this regard, the thickness of the sheet may vary according to the concentration of the monomer composition fed thereto and the feeding speed, and the polymer sheet is preferably controlled to have a thickness of 0.5 to 5 cm in order to uniformly polymerize the entire sheet and secure production speed.

The water-containing gel polymer formed by the above method may have a water content of about 40% by weight to 80% by weight. The "water content", as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the drying conditions are determined as follows; the temperature is increased from room temperature to about 180° C. and then the temperature is maintained at 180° C., and the total drying time is determined as 20 minutes, including 5 minutes for the temperature rising step.

Step of Drying the Water-Containing Gel Polymer (Step 2)

Meanwhile, the method of preparing the superabsorbent polymer includes the step of drying the water-containing gel polymer which is formed by the above described step.

If necessary, the method may further include the step of (coarsely) pulverizing the water-containing gel polymer before drying, in order to increase efficiency of the drying step.

A non-limiting example of a pulverizing device applicable to the coarse pulverization may include a vertical pulverizer, a turbo cutter, a turbo grinder, a rotary cutter mill, a cutter mill, a disc mill, a shred crusher, a crusher, a chopper, a disc cutter, etc.

In this regard, the coarse pulverization may be performed so that the water-containing gel polymer has a particle size of about 2 mm to about 10 mm. That is, to increase the drying efficiency, the water-containing gel polymer is preferably pulverized to have a particle size of 10 mm or less. However, excessive pulverization may cause agglomeration between particles, and therefore, the water-containing gel polymer is preferably pulverized to have a particle size of 2 mm or more.

When the coarse pulverization is performed before the step of drying the water-containing gel polymer, the polymer may stick to the surface of the pulverizing device because it has high water content. In order to minimize this phenomenon, steam, water, a surfactant, an anti-agglomeration agent such as clay or silica, etc.; a thermal polymerization initiator such as a persulfate-based initiator, an azo-based initiator, hydrogen peroxide, and ascorbic acid; or a crosslinking agent such as an epoxy-based crosslinking agent, a diol-based crosslinking agent, a crosslinking agent including 2-functional or 3 or more-functional acrylate, a monofunctional compound including a hydroxyl group may be added during the coarse pulverization step.

The drying of the water-containing gel polymer immediately after coarse pulverization or polymerization may be performed at a temperature of 120° C. to 250° C., preferably 150° C. to 200° C., and more preferably 160° C. to 180° C. (In this regard, the temperature means the temperature of the heating medium provided thereto for drying, or the internal temperature of the drying reactor including the heating medium and the polymer during the drying process). If the drying temperature is low, and therefore the drying time becomes long, physical properties of the final polymer may be deteriorated. In order to prevent this problem, the drying temperature is preferably 120° C. or higher. In addition, when the drying temperature is higher than necessary, only the surface of the water-containing gel polymer is excessively dried, and thus there is a concern about generation of fine powder during the subsequent pulverization process and deterioration of the physical properties of the polymer finally formed. In order to prevent this problem, therefore, the drying temperature is preferably 250° C. or lower.

In this regard, the drying time in the drying step is not particularly limited, but may be controlled to 20 to 90 minutes at the above drying temperature, in consideration of the process efficiency.

A drying method in the drying step may be also a method generally used in the drying process of the water-containing gel polymer, and there is no limitation in the constitution. Specifically, the drying step may be carried out by a method of supplying hot air, irradiating infrared rays, irradiating microwaves, irradiating ultraviolet rays, or the like.

The water content of the polymer dried by the above method may be about 0.1% by weight to about 10% by weight. In other words, if the water content of the polymer is less than 0.1% by weight, production costs may be increased due to excessive drying and degradation of the crosslinked polymer may occur, undesirably. If the water content of the polymer is more than 10% by weight, defective products may be undesirably produced in the subsequent process.

Step of Pulverizing the Dried Polymer (Step 3)

Meanwhile, the method of preparing the superabsorbent polymer includes the step of pulverizing the polymer which is dried by the above-described step.

The pulverization step is a step of optimizing the surface area of the dried polymer, and the step is performed to make the pulverized polymer have a particle diameter of 150 μm to 850 μm. In this regard, a pulverization device applicable to the pulverization for such particle size may be exemplified by a pin mill, a hammer mill, a screw mill, a roll mill, a disc mill, a jog mill or the like.

Further, a step of selectively size-sorting the polymer particles obtained through the process into the polymer having a particle diameter of 150 μm to 850 μm may be further performed in order to manage physical properties of the superabsorbent polymer finally produced.

Step of Surface-Crosslinking the Pulverized Polymer (Step 4)

Meanwhile, the method of preparing the superabsorbent polymer includes the step of surface-crosslinking the polymer which is pulverized by the above-described step.

The surface crosslinking is a method of increasing crosslinking density of the surface of the polymer particle, and for example, a solution including the crosslinking agent (surface crosslinking agent) is mixed with the pulverized polymer to allow crosslinking reaction.

Herein, the crosslinking agent (surface crosslinking agent) included in the surface crosslinking solution may be a compound having two or more epoxy rings. Since the epoxy ring is able to react with a carboxylic group present on the surface of the superabsorbent polymer, and two or more epoxy rings exist in the crosslinking agent, a multiple crosslinking structure may be prepared on the surface of the superabsorbent polymer by the crosslinking agent, thereby increasing the surface crosslinking density. Accordingly, gel bed permeability of the superabsorbent polymer may be improved.

Preferably, the compound having two or more epoxy rings may be a compound represented by the following Chemical Formula 2:

[Chemical Formula 2]

wherein, $R_2$ is $C_{1-3}$ alkylene.

In this regard, the content of the surface crosslinking agent may be properly controlled according to the type of the crosslinking agent or reaction conditions, and the content is preferably 0.001 parts by weight to 5 parts by weight, based on 100 parts by weight of the pulverized polymer. If the content of the surface crosslinking agent is too low, surface crosslinking may hardly occur to deteriorate physical properties of the final polymer. On the contrary, if the surface crosslinking agent is excessively used, excessive surface crosslinking reaction may occur, leading to deterioration in absorption ability of the polymer.

Further, the surface crosslinking reaction may be performed by using silica, in addition to the compound having two or more epoxy rings.

When silica particles are used together, the surface of the superabsorbent polymer may be coated with silica particles. In general, silica particle coating may improve gel bed permeability of the superabsorbent polymer, but tend to decrease absorbency under load (AUL) and suction power thereof. In the present invention, however, surface crosslinking reaction is performed by using the compound having two or more epoxy rings, thereby improving absorbency under load (AUL) and suction power as well as improving gel bed permeability by use of silica.

Further, the surface crosslinking reaction may be performed by using polyol together with the compound having two or more epoxy rings. Use of polyol aids the surface crosslinking reaction, thereby improving physical properties of the superabsorbent polymer. Examples of the polyol may include ethylene glycol, diethylene glycol, propylene glycol, triethylene glycol, tetraethylene glycol, propane diol, dipropylene glycol, polypropylene glycol, glycerin, polyglycerin, butanediol, heptanediol, hexanediol, trimethylol propane, pentaerythritol, and sorbitol.

Meanwhile, the surface crosslinking step may be performed by a method of feeding the surface crosslinking solution and the pulverized polymer to the reactor and mixing them, a method of spraying the surface crosslinking solution to the pulverized polymer, or a method of mixing the pulverized polymer and the surface crosslinking solution while continuously feeding them to a mixer being continuously operated.

The surface crosslinking agent may be added with water. When the surface crosslinking agent is added together with water, the crosslinking agent may be evenly dispersed, agglomeration of the polymer powder may be prevented, and the penetrating depth of the surface crosslinking agent into the polymer powder may be optimized. Considering these purposes and effects, the amount of water to be added may be 0.5 parts by weight to 10 parts by weight, based on 100 parts by weight of the pulverized polymer.

The surface crosslinking step may be preferably performed at a temperature of 170° C. to 250° C. If the temperature is lower than 170° C., sufficient surface crosslinking of the superabsorbent polymer may not occur by the compound having two or more epoxy rings.

Further, the surface crosslinking reaction may be performed for 50 minutes or longer. That is, in order to induce the minimal surface crosslinking reaction and to prevent a reduction in physical properties due to deterioration in the polymer particles during excessive reaction, the surface crosslinking reaction may be performed under the above described conditions. Further, the reaction may be performed for 120 minutes or shorter. 100 minutes or shorter, or 60 minutes or shorter.

EFFECT OF THE INVENTION

The superabsorbent polymer according to the present invention has excellent gel bed permeability (GBP) and suction power, thereby being usefully applied to hygiene products such as diapers.

DETAILED DESCRIPTION OF THE EMBODIMENTS

Hereinafter, the preferred examples are provided for better understanding. However, these examples are for illustrative purposes only, and the present invention is not intended to be limited by these examples.

EXAMPLE 1-1

A partially neutralized acrylic acid aqueous solution was mixed with 3000 ppm of PEGDA (polyethylene glycol diacrylate) as an internal crosslinking agent, 30 ppm of Irgacure 819 (Bis(2,4,6-trimethylbenzoyl)-phenylphosphineoxide) as a photoinitiator, and 1000 ppm of sodium persulfonate (SPS) as a thermal initiator, and then light irradiation was performed for 1 minute to obtain a polymerized sheet. The polymerized sheet was taken and cut in a size of 3 cm×3 cm and then subjected to a chopping process using a meat chopper to prepare crumbs. The crumbs were dried in an oven capable of shifting airflow up and down. The crumbs were uniformly dried by flowing hot air at 180° C. from the bottom to the top for 15 minutes and from the top to the bottom for 15 minutes. After drying, the dried product had a water content of 2% or less. After drying, the product was pulverized using a pulverizer and sorted by size, and a size of about 150 to about 850 μm was selected to prepare a base polymer. Thereafter, based on 100 g of the base polymer, 3% water, 3% methanol, 0.1% epoxy compound (ethyleneglycol diglycidyl ether), and 0.06% silica Aerosil 200 were mixed, and then reaction was allowed for 1 hour while raising temperature from 170° C. to 195° C. After pulverization, a surface-treated superabsorbent polymer having a particle size of 150 μm to 850 μm was obtained by using a sieve.

EXAMPLE 1-2

A superabsorbent polymer was prepared in the same manner as in Example 1-1, except that 0.08% silica Aerosil was applied upon surface crosslinking.

EXAMPLE 1-3

A superabsorbent polymer was prepared in the same manner as in Example 1-1, except that 0.10% silica Aerosil was applied upon surface crosslinking.

EXAMPLE 1-4

A superabsorbent polymer was prepared in the same manner as in Example 1-1, except that 0.12% silica Aerosil was applied upon surface crosslinking.

EXAMPLE 1-5

A superabsorbent polymer was prepared in the same manner as in Example 1-1, except that 0.14% silica Aerosil was applied upon surface crosslinking.

EXAMPLE 1-6

A superabsorbent polymer was prepared in the same manner as in Example 1-1, except that 0.16% silica Aerosil was applied upon surface crosslinking.

EXAMPLE 2-1

A partially neutralized acrylic acid aqueous solution was mixed with 4500 ppm of PEGDA(polyethylene glycol diacrylate) as an internal crosslinking agent, 30 ppm of Irgacure 819 (Bis(2,4,6-trimethylbenzoyl)-phenylphosphineoxide) as a photoinitiator, and 1000 ppm of sodium persulfonate (SPS) as a thermal initiator, and then light irradiation was performed for 1 minute to obtain a polymerized sheet. The polymerized sheet was taken and cut in a size of 3 cm×3 cm and then subjected to a chopping process using a meat chopper to prepare crumbs. The crumbs were dried in an oven capable of shifting airflow up and down. The crumbs were uniformly dried by flowing hot air at 180° C. from the bottom to the top for 15 minutes and from the top to the bottom for 15 minutes. After drying, the dried product had a water content of 2% or less. After drying, the product was pulverized using a pulverizer and sorted by size, and a size of about 150 to about 850 μm was selected to prepare a base polymer. Thereafter, based on 100 g of the base polymer, 3% water, 3% methanol, 0.1% epoxy compound (ethyleneglycol diglycidyl ether), and 0.06% silica Aerosil 200 were mixed, and then reaction was allowed for 1 hour while raising temperature from 170° C. to 195° C. After pulverization, a surface-treated superabsorbent polymer having a particle size of 150 μm to 850 μm was obtained by using a sieve.

EXAMPLE 2-2

A superabsorbent polymer was prepared in the same manner as in Example 2-1, except that 0.04% silica Aerosil was applied upon surface crosslinking.

EXAMPLE 2-3

A superabsorbent polymer was prepared in the same manner as in Example 2-1, except that 0.06% silica Aerosil was applied upon surface crosslinking.

EXAMPLE 2-4

A superabsorbent polymer was prepared in the same manner as in Example 2-1, except that 0.08% silica Aerosil was applied upon surface crosslinking.

EXAMPLE 2-5

A superabsorbent polymer was prepared in the same manner as in Example 2-1, except that 0.10% silica Aerosil was applied upon surface crosslinking.

EXAMPLE 2-6

A superabsorbent polymer was prepared in the same manner as in Example 2-1, except that 0.12% silica Aerosil was applied upon surface crosslinking.

COMPARATIVE EXAMPLE 1-1

A superabsorbent polymer was prepared in the same manner as in Example 1-1, except that reaction temperature was 120° C. upon surface crosslinking.

COMPARATIVE EXAMPLE 1-2

A superabsorbent polymer was prepared in the same manner as in Example 1-1, except that reaction temperature was 120° C. and 0.08% silica Aerosil was applied upon surface crosslinking.

COMPARATIVE EXAMPLE 1-3

A superabsorbent polymer was prepared in the same manner as in Example 1-1, except that reaction temperature was 120° C. and 0.10% silica Aerosil was applied upon surface crosslinking.

COMPARATIVE EXAMPLE 2-1

A superabsorbent polymer was prepared in the same manner as in Example 2-1, except that reaction temperature was 120° C. upon surface crosslinking.

COMPARATIVE EXAMPLE 2-2

A superabsorbent polymer was prepared in the same manner as in Example 2-1, except that reaction temperature was 120° C. and 0.04% silica Aerosil was applied upon surface crosslinking.

EXPERIMENTAL EXAMPLE

Physical properties of the superabsorbent polymers prepared in Examples and Comparative Examples were evaluated as follows.

(1) Gel Bed Permeability (GBP)

Gel bed permeability (GBP) was measured for the superabsorbent polymers prepared in Examples and Comparative Examples. A method of measuring GBP is described in U.S. Pat. No. 7,179,851.

Figure 1:
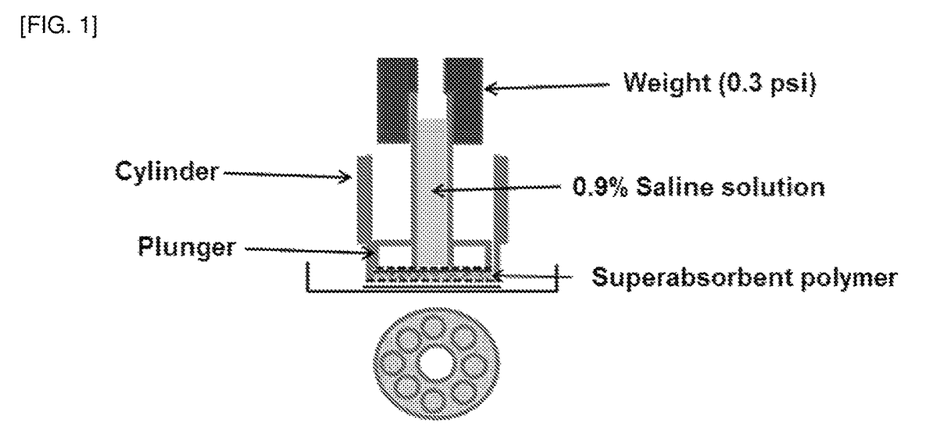
FIG. 1 illustrates an example of an apparatus for measuring absorption rate under load of a superabsorbent polymer according to an embodiment of the present invention.
Figure 2:
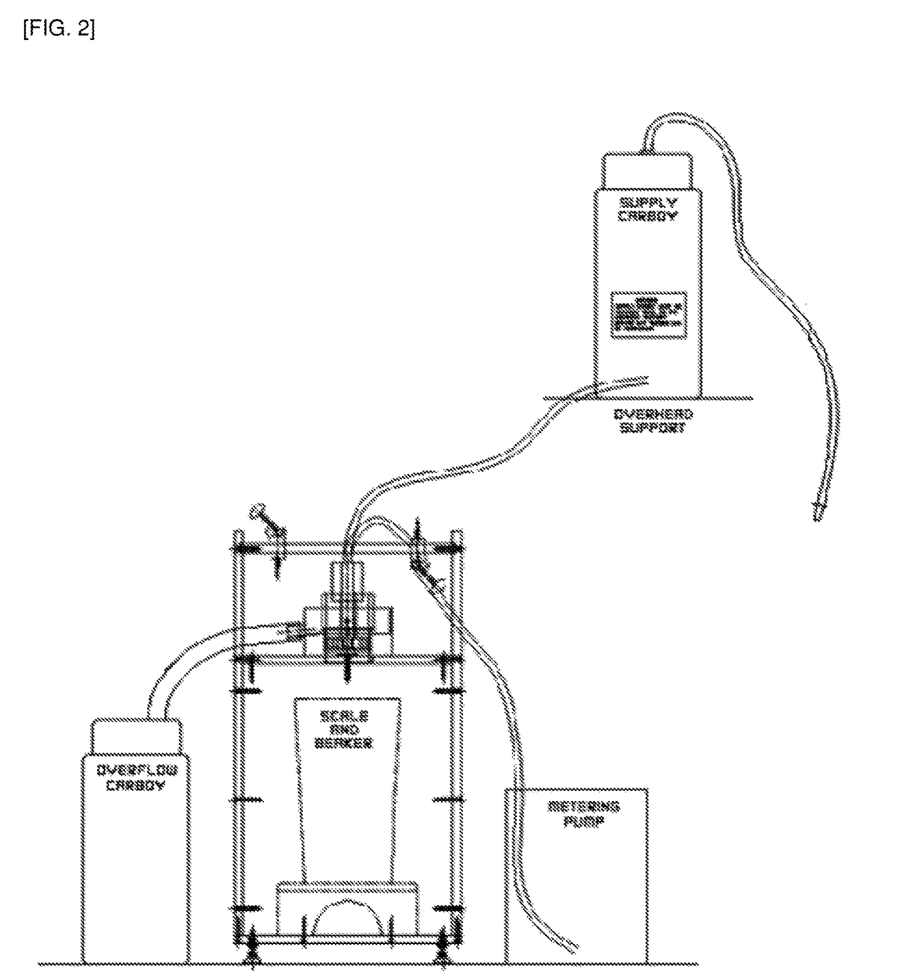
FIG. 2 illustrates an example of an apparatus for measuring gel bed permeability (GBP) according to an embodiment of the present invention.
Figure 3:
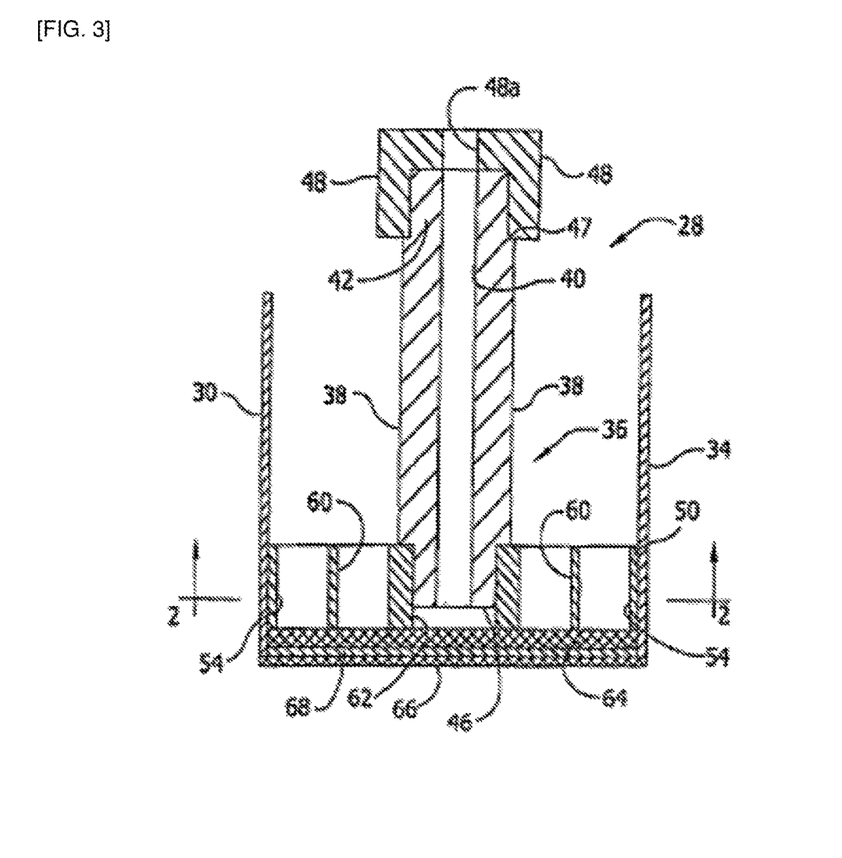
FIGS. 3 and 4 illustrate an example of a cylinder and a mesh arrangement for measuring gel bed permeability.
Figure 4:
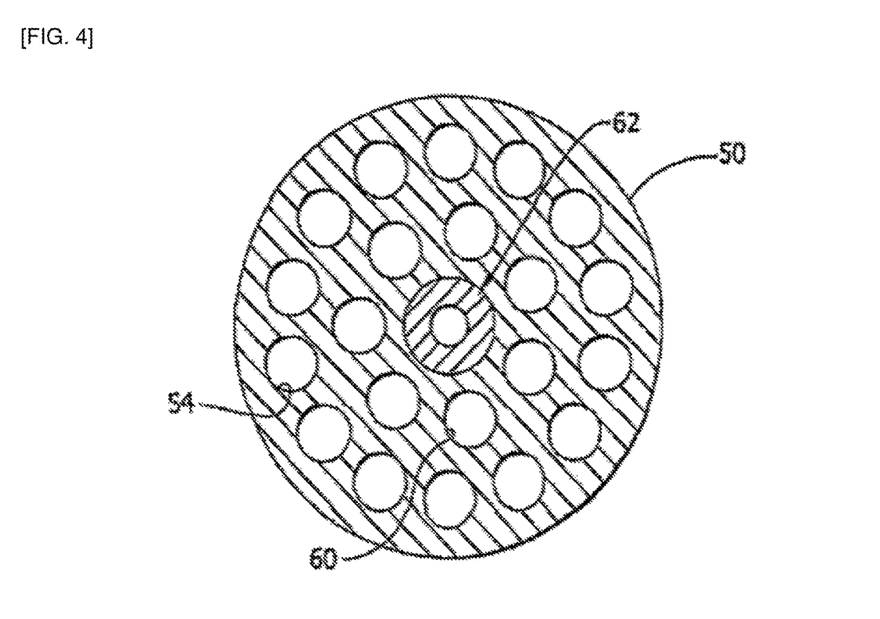

First, a suitable apparatus for conducting a gel bed permeability test is illustrated in FIG. 2, and detail thereof is illustrated in FIGS. 3 and 4. The test apparatus 28 includes a sample container (generally indicated by 30) and a piston (generally indicated by 35). The piston 35 includes a cylindrical LEXAN® shaft 38 having a concentric cylindrical hole 40 bored down the longitudinal axis of the shaft. Both ends of the shaft 38 are machined to provide upper and lower ends (indicated by 42 and 46, respectively). A weight (indicated by 48) rests on one end 42 and has a cylindrical hole 48a bored through at least a portion of its center.

A circular piston head 50 is positioned on the other end 46 and is provided with a concentric inner ring of seven holes 60 (each having a diameter of about 0.95 cm), and a concentric outer ring of fourteen holes 54 (each having a diameter of about 0.95 cm). The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64.

The sample container 30 includes a cylinder 34 and a 400 mesh stainless steel cloth screen 66 that is biaxially stretched to tautness and attached to the lower end of the cylinder. A superabsorbent polymer sample (indicated by 68 in FIG. 3) is supported on the screen 66 within the cylinder 34 during testing.

The cylinder 34 may be bored from a transparent LEXAN rod of equivalent material, or it may be cut from a LEXAN tubing or equivalent material, and has an inner diameter of about 6 cm (e.g., a cross sectional area of about 28.27 cm$^2$), a wall thickness of about 0.5 cm and a height of about 10 cm. Drainage holes (not shown) are formed in the sidewall of the cylinder 34 at a height of about 7.8 cm above the screen 66 to allow liquid to drain from the cylinder, thereby maintaining a fluid level in the sample container at about 7.8 cm above screen 66. The piston head 50 is machined from a LEXAN rod or equivalent material and has a height of about 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is about 2.54 cm long and about 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 may be made from stainless steel or from other suitable materials resistant to corrosion in the presence of the test solution, which is 0.9% by weight of sodium chloride solutions in distilled water. The combined weight of the piston 35 and annular weight 48 equals about 596 g, which corresponds to a pressure applied to the absorbent structure sample 68 of about 0.3 psi, or about 20.7 g/cm$^2$, over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the gel bed permeability test under free swell conditions, the piston 35, with the weight 48 seated thereon, is placed in an empty sample container 30 and the height from the bottom of the weight 48 to the top of the cylinder 34 is measured using a calliper of suitable gauge accurate to 0.01 mm. It is important to measure the height of each sample container 30 empty and to keep track of which piston 35 and weight 48 is used when using a multiple test apparatus. The same piston 35 and weight 48 should be used for measurement when the superabsorbent polymer sample 68 is water swollen following saturation.

The sample to be tested is prepared from superabsorbent material particles which are prescreened through a US standard 30 mesh screen and retained on a US standard 50 mesh screen. As a result, the test sample includes particles sized in the range of about 300 to about 600 μm. The particles may be prescreened by hand or automatically. About 2.0 g of the sample is placed in the sample container 30, and the container, without the piston 35 and weight 48 therein, is then submerged in the test solution for a time period of about 60 minutes to saturate the sample and allow the sample to swell free of any restraining load.

At the end of this period, the piston 35 and the weight 48 are placed on the saturated sample 68 in the sample container 30 and then the sample container 30, piston 35, weight 48, and sample 68 are removed from the solution. The thickness of the saturated sample 68 is determined by again measuring the height from the bottom of the weight 48 to the top of the cylinder 34, using the same calliper or gauge used previously (provided that the zero point is unchanged from the initial height measurement). The height measurement obtained from measuring the empty sample container 30, piston 35, and weight 48 is subtracted from the height measurement obtained after saturating the sample 48. The resulting value is the thickness or height "H" of the swollen sample.

The permeability measurement is initialed by delivering a flow of the test solution into the sample container 30 with the saturated sample 68, piston 35, and weight 48 inside. The flow rate of test solution into the container is adjusted to maintain a fluid height of about 7.8 cm above the bottom of the sample container. The quantity of solution passing through the sample 68 versus time is measured gravimetrically. Data points are collected every second for at least 20 seconds once the fluid level has been stabilized to and maintained at about 7.8 cm in height. The flow rate Q through the swollen sample 68 is determined in units of g/s by a linear least-square fit of fluid passing through the sample 68 (g) versus time (sec).

Permeability (Darcy) is obtained by the following Equation 3:

$$K=[Q \times H \times Mu]/[A \times Rho \times P] \quad \text{[Equation 2]}$$

wherein, K is a permeability (cm$^2$), Q is a flow rate (g/rate), H is a height of the sample (cm), Mu is a liquid viscosity (poise) (approximately 1 cps for the test solution used in the test), A is a cross-sectional area for liquid flow (cm$^2$), Rho is a liquid density (g/cm$^3$) (for the test solution used in this test) and P is a hydrostatic pressure (dynes/cm$^2$) (normally approximately 3.923 dynes/cm$^2$). The hydrostatic pressure is calculated from the following Equation 3:

$$P = Rho \times g \times h \quad \text{[Equation 3]}$$

wherein, Rho is a liquid density (g/cm$^2$), g is gravitational acceleration, nominally 981 cm/sec$^2$, and h is a fluid height (e.g., 7.8 cm for the permeability test described herein).

(2) Absorbency Under Load (AUL)

Absorbency under load (AUL) at 0.9 psi was measured for the superabsorbent polymers prepared in Examples and Comparative Examples by the following method.

First, a 400 mesh stainless steel net was installed in the bottom of the plastic cylinder having the internal diameter of 25 mm. Each of the superabsorbent polymers $W_0(g)$ (0.16 g) was uniformly scattered on the steel net at room temperature and the humidity of 50%, and a piston which may provide a load of 5.1 kPa (0.9 psi) uniformly was put thereon, in which the external diameter of the piston was slightly smaller than 25 mm, there was no gab between the internal wall of the cylinder and the piston, and the jig-jog of the cylinder was not interrupted. At this time, the weight $W_3(g)$ of the device was measured.

After putting a glass filter having a diameter of 90 mm and a thickness of 5 mm in a petri dish having a diameter of 150 mm, a physiological saline solution composed of 0.90% by weight of sodium chloride was poured in the dish until the surface level became equal to the upper surface of the glass filter. A sheet of filter paper having a diameter of 90 mm was put thereon. The measuring device was put on the filter paper and the solution was absorbed for 1 hour under the load. After 1 hr, the weight $W_4(g)$ was measured after lifting the measuring device up.

The weights thus obtained were used to calculate AUL (g/g) according to the following Equation 4:

$$AUL(g/g)=[W_4(g)-W_3(g)]/W_0(g) \quad \text{[Equation 4]}$$

wherein, $W_0(g)$ is the weight (g) of the superabsorbent polymer, $W_3(g)$ is the sum (g) of the weight of the superabsorbent polymer and the weight of the apparatus capable of providing a load for the superabsorbent polymer, and $W_4(g)$ is the sum (g) of the weight of the water-absorbed superabsorbent polymer after supplying water for the superabsorbent polymer under a load (0.9 psi) for 1 hour and the weight of the apparatus capable of providing a load for the superabsorbent polymer.

(3) Suction Power (SP)

An apparatus as in FIG. 5 was used to measure SR In detail, a saline solution (0.9% NaCl) was poured to 0 ml gradation mark of a glass tube having an internal diameter of 20 mm on the right of a measuring device. A 100-micrometer glass filter was placed on the bottom of a cylindrical funnel having an internal diameter of 50 mm on the left of the measuring device, and 1.0 g of the superabsorbent polymer was uniformly scattered on the glass filter at 23° C. and the relative humidity of 50%. While the superabsorbent polymer was scattered, the amount of saline solution absorbed into 1 g of the superabsorbent polymer for 5 minutes was measured by opening a tap of a burette of the measuring device.

Results of the measurement are given in the following Tables 1 and 2.

TABLE 1

| | Silica (wt %) | GBP (Darcy) | 0.9AUL (g/g) | S.P (g/g) |
|---|---|---|---|---|
| Example 1-1 | 0.06 | 45 | 21.9 | 15.9 |
| Example 1-2 | 0.08 | 46 | 18.7 | 14.1 |
| Example 1-3 | 0.10 | 48 | 18.5 | 14.2 |
| Example 1-4 | 0.12 | 55 | 18.4 | 13.7 |
| Example 1-5 | 0.14 | 57 | 17.7 | 13.6 |
| Example 1-6 | 0.16 | 61 | 17.3 | 13.4 |
| Comparative Example 1-1 | 0.06 | 22 | 21.4 | 14.5 |
| Comparative Example 1-2 | 0.08 | 31 | 18.9 | 14.0 |
| Comparative Example 1-3 | 0.10 | 34 | 17.3 | 13.9 |

TABLE 2

| | Silica (wt %) | GBP (Darcy) | 0.9AUL (g/g) | S.P (g/g) |
|---|---|---|---|---|
| Example 2-1 | 0.02 | 41 | 21.9 | 16.2 |
| Example 2-2 | 0.04 | 64 | 21.2 | 14.8 |
| Example 2-3 | 0.06 | 88 | 20.6 | 14.5 |
| Example 2-4 | 0.08 | 92 | 19.7 | 14.1 |
| Example 2-5 | 0.10 | 115 | 19.0 | 13.9 |
| Example 2-6 | 0.12 | 125 | 19.1 | 13.5 |
| Comparative Example 2-1 | 0.02 | 23 | 22.0 | 14.5 |
| Comparative Example 2-2 | 0.04 | 36 | 21.9 | 14.0 |

The invention claimed is:

1. A super absorbent polymer, comprising a base polymer comprising a crosslinked polymer of water-soluble ethylene-based unsaturated monomers having acidic groups which are at least partially neutralized, and a surface crosslinked layer comprising the additionally crosslinked polymer of the base polymer, which is formed on the base polymer, wherein suction power of 1 g of the superabsorbent polymer for 5 minutes is 13 mL/g or more and gel bed permeability (GBP) of the superabsorbent polymer is 41 Darcy or more.

2. The super absorbent polymer of claim 1, wherein absorbency under load (AUL) at 0.9 psi of the superabsorbent polymer is 17.3 g/g or more.

3. The super absorbent polymer of claim 1, wherein the water-soluble ethylene-based unsaturated monomer is a compound represented by the following Chemical Formula 1:

$$R_1\text{---}COOM^1 \quad \text{[Chemical Formula 1]}$$

wherein,
$R_1$ is an alkyl group containing an unsaturated bond and having 2 to 5 carbon atoms, and
$M^1$ is a hydrogen atom, a monovalent or divalent metal, an ammonium group, or an organic amine salt.

4. The super absorbent polymer of claim 1, wherein the water-soluble ethylene-based unsaturated monomer comprises one or more selected from the group consisting of an anionic monomer such as acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth) acrylamide, N-substituted (meth)acrylate, 2-hydroxyethyl (meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylamide, and a quaternary compound thereof.

5. A method of preparing the superabsorbent polymer of claim 1, the method comprising the steps of:
   1) performing thermal polymerization or photo-polymerization of a monomer composition comprising water-soluble ethylene-based unsaturated monomers and a polymerization initiator to form a water-containing gel polymer,
   2) drying the water-containing gel polymer,
   3) pulverizing the dried polymer, and
   4) surface-crosslinking the pulverized polymer by reacting the pulverized polymer with a compound having two or more epoxy rings at 170 to 250° C. for 50 minutes or longer.

6. The method of claim 5, wherein Step 1 is performed in the presence of one or more internal crosslinking agents selected from the group consisting of polyethylene glycol diacrylate (PEGDA), glycerin diacrylate, glycerin triacrylate, non-modified or ethoxylated trimethylol propane triacrylate (TMPTA), hexanediol diacrylate, and triethylene glycol diacrylate.

7. The method of claim 5, further comprising the step of pulverizing the water-containing gel polymer to a particle diameter of 2 to 10 mm before drying of the water-containing gel polymer.

8. The method of claim 5, wherein pulverization of the dried polymer is performed to make the pulverized polymer have a particle diameter of 150 to 850 µm.

9. The method of claim 5, wherein the compound having two or more epoxy rings is a compound represented by the following Chemical Formula 2:

[Chemical Formula 2]

wherein,
$R_2$ is $C_{1\text{-}3}$ alkylene.

10. The method of claim 5, wherein the surface crosslinking reaction is performed by using silica.

11. The method of claim 5, wherein the surface crosslinking reaction is performed by using silica or polyol.

12. The method of claim 11, wherein the polyol is ethylene glycol, diethylene glycol, propylene glycol, triethylene glycol, tetraethylene glycol, propane diol, dipropylene glycol, polypropylene glycol, glycerin, polyglycerin, butanediol, heptanediol, hexanediol, trimethylol propane, pentaerythritol, or sorbitol.

* * * * *